United States Patent [19]

Sheridan et al.

[11] Patent Number: 4,873,876
[45] Date of Patent: Oct. 17, 1989

[54] CHEMICAL PROCESS SAMPLER

[75] Inventors: Michael Sheridan, Old Bridge, N.J.; Kenneth Jaffe, Boulder, Colo.

[73] Assignee: Ethylene Corp., Murray Hill, N.J.

[21] Appl. No.: 267,984

[22] Filed: Nov. 7, 1988

[51] Int. Cl.⁴ .............................................. G01N 1/20
[52] U.S. Cl. ................................ 73/863.86; 73/863.73
[58] Field of Search ......................... 73/823.86, 863.73

[56] References Cited

U.S. PATENT DOCUMENTS

| | | |
|---|---|---|
| 4,174,632 | 11/1979 | Jansen . |
| 4,195,525 | 4/1980 | George et al. ................... 73/863.73 |
| 4,252,021 | 2/1981 | Drushel . |
| 4,454,774 | 6/1984 | Pridgen ............................ 73/863.81 |
| 4,472,977 | 9/1984 | Lynn ............................ 73/863.73 X |
| 4,562,748 | 1/1986 | Mrochek et al. ................ 73/863.73 |
| 4,578,244 | 3/1986 | Cosgrove et al. .................... 422/65 |
| 4,580,452 | 5/1986 | Masson ............................. 73/863.86 |
| 4,651,574 | 3/1987 | Spencer ............................ 73/863.86 |
| 4,669,321 | 6/1987 | Meyer ............................... 73/863.85 |
| 4,702,114 | 11/1987 | Cabannes ......................... 73/863.85 |
| 4,736,636 | 4/1988 | Fini et al. ........................ 73/863.73 |

FOREIGN PATENT DOCUMENTS

| | | | |
|---|---|---|---|
| 200795 | 8/1967 | U.S.S.R. | ............................ 73/863.86 |
| 1076695 | 2/1984 | U.S.S.R. | ............................ 73/863.86 |
| 1318834 | 6/1987 | U.S.S.R. | ............................ 73/863.86 |

Primary Examiner—Tom Noland
Attorney, Agent, or Firm—Charles E. Temko

[57] ABSTRACT

A chemical process sampler for use in monitoring the progress of chemical processing particularly suited for the handling of toxic, volatile, or otherwise dangerous substances. The sampler is characterized in the provision of multi-position valve structure for returning a contained sample to the processing vessel after use, thereby eliminating the need for separate disposal.

9 Claims, 7 Drawing Sheets

NEUTRAL PRESSURE RELEASE

FIG. 13.

BOTTLE & VALVE PURGE

FIG. 11.

SAMPLE

FIG. 14.

PRESSURE RELEASE

FIG. 12.

COMPRESSED AIR SUPPLY

SAMPLE RETURN

FIG. 15.

BOTTLE REMOVAL

CHEMICAL PROCESS SAMPLER

BACKGROUND OF THE INVENTION

This invention relates generally to the field of chemical processing, particularly of toxic, volatile or otherwise dangerous substances, and more particularly to an improved process sampler by means of which small quantities of substances to be examined may be removed from a reacting mass for analysis at convenient intervals during a processing cycle. Devices of this general type are known in the art, and the invention lies in specific constructional details which afford increased convenience with regard to the recycling of a tested sample, and more importantly, increased safety to the technician or operator conducting the sampling operation.

The need for obtaining uncontaminated representative samples of chemical processing operations has been one of long standing. The most common method employed involves the use of a so-called dip tube which is projected through or mounted within an orifice in the reactor vessel. Where the sampled material is not particularly dangerous, this structure has proved adequate.

More sophisticated sampling devices include those sold under the trademark DOPAK. These devices include a means for connecting into the process line at a suitable point which means includes a valve to control flow to a sample container. Adjacent the valve is a pair of hollow needles both of which penetrate a self-sealing diaphragm or septum located beneath the threaded cap of the sample container. One needle feeds the sample, while the other needle exhausts air or other displaced fluid within the container. When the container is filled with a sample to desired volume, the container is disconnected from the needles without spillage.

Another type of sampling device is marketed under the trademark POSACON. This type of device is installed in line with a conduit, and includes a transversely arranged needle valve which communicates with a selectively engageable piston injector which operates somewhat in the manner of a hypodermic syringe. The injector has means for closing the same against leakage before disconnecting from the valve body.

In both types of devices, above-described, after examination and/or testing of the sample, there remains the problem of disposing of the unused portion thereof which may create environmental problems, particularly where the samples are corrosive, toxic, or otherwise dangerous.

SUMMARY OF THE INVENTION

Briefly stated, the invention contemplates the provision of an improved device of the class described having means for returning a sample substance to the process line or vessel, thereby eliminating the need for subsequent disposal. To this end, the disclosed embodiment includes an in-line sampling valve controlling the operation of a housing element which defines a recess selectively receiving the mouth of a sampling container for communication therebetween. The housing and container are provided with filling and venting passages, and an interlocking mechanism actuated upon engagement of the container prevents the opening of the passages until the container is fully seated within the housing. Removal of the container automatically closes the passages in the container. The interlock mechanism prevents removal of the container until the sampling valve has been placed in a position preventing further communication therewith. When the remaining contents of the container are to be returned to the process line, the container is reengaged and the valve opened to a return position to enable flow from the container to the process line, while simultaneously preventing flow from the process line to the container. Where the process line has sufficient suction, the container is readily emptied. If sufficient reduced pressure is not present, nitrogen gas or similar inert fluid, under pressure, is introduced into the container to accomplish the same purpose.

The above-described structure provides a number of advantages not available in prior art construction. The filling and venting passages allow conditioning of the sample container by providing a dedicated pair of connections for the establishment of a flow path through the sample container before the sample is taken. Since the flow of process stream is partially diverted through the sample container, the container may fill to a predetermined level without operator influence. The flow can be maintained for an indefinite period of time, thus providing a pure representative sample.

As contrasted with needle-type samplers, the structure of the disclosed embodiment allows sampling of slurries containing particles up to one-half inch diameter without affecting either the valve or sample container seals. The contents of the sample container can be either pulled or blown back into the process stream, depending upon the availability of process line pressure. Should the sample container be absent, or improperly installed by the operator, operator safety is maintained by the nature of the operation of the locking valve structure.

To provide still further safety, an optional sample container enclosure may be incorporated to provide a sealed purged buffer between the operator and the sample container should a leak develop. If desired, means may also be provided to ensure that the enclosure door is closed during the period in which the sample container is being filled or emptied. The sample container itself is provided with a rotary closure which prevents the escape of harmful vapors or fluid when in detached condition. This closures maintains a closed system within the container at all times during normal operations.

BRIEF DESCRIPTION OF THE DRAWINGS

In the drawings, to which reference will be made in the specification, similar reference characters have been employed to designate corresponding parts throughout the several views.

DETAILED DESCRIPTION OF THE DISCLOSED EMBODIMENT

In accordance with the invention, the device, generally indicated by reference character 10, comprises: a housing element 11 including first and second flange members 12 and 13 which are directly interconnected in a process line 13A and a centrally positioned valve body 14 including an outer shell 15 enclosing a transversely extending chamber 16. The chamber communicates with a main conduit 17 and is closed by an orifice cover 18 accommodating a shaft 19 driving a rotating valve spool 20. The housing forms a mounting surface 21 having a plurality of tapped bores 22 surrounding inlet and outlet passages 23 and 24, which, in assembled condition, communicate with a container engaging element 25.

Figure 4:
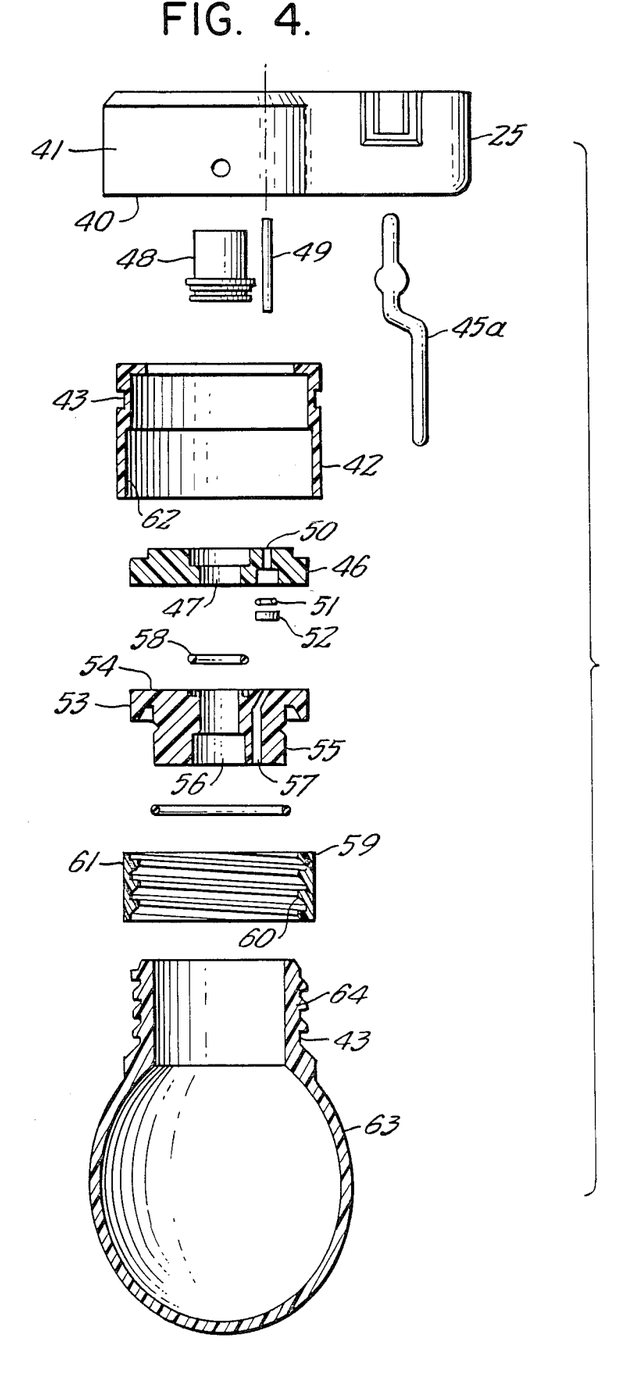
FIG. 4 is an exploded view in elevation, partly in section, showing details of a sample container engaging structure.
Figure 5:
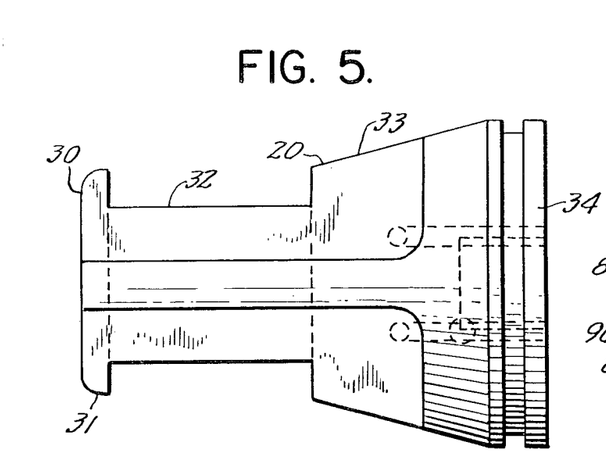
FIG. 5 is a top plan view of a valve spool comprising a part of the disclosed embodiment.

The valve spool 20 is most conveniently formed as a casting of chemically inert materials, and is of generally tapered outer configuration (see FIGS. 4 and 5). An end wall 30 provides a peripheral sealing surface 31 adjacent a passage forming area 32 bounded on an opposite end by a conically shaped member 33 which declines a recess 34 engageable with the inner end of the shaft 19. The shaft 19 has a spline 35 on a first end 36 engaging the recess 34.

Figure 10:
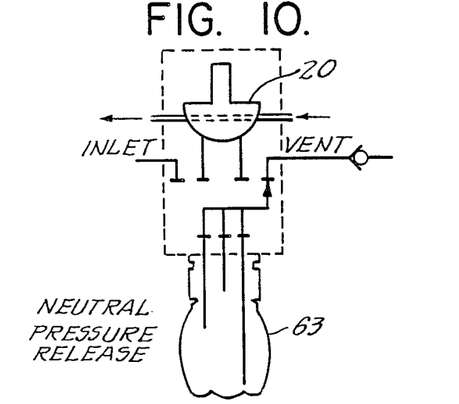
FIG. 10 is a schematic view of the embodiment showing normal operation and venting of a sample container.
Figure 11:
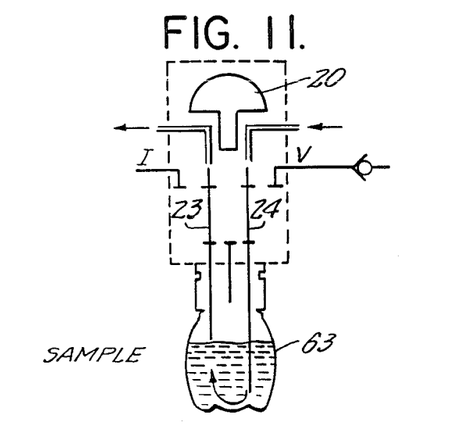
FIG. 11 is a similar schematic view showing the filling of a sample container.
Figure 12:
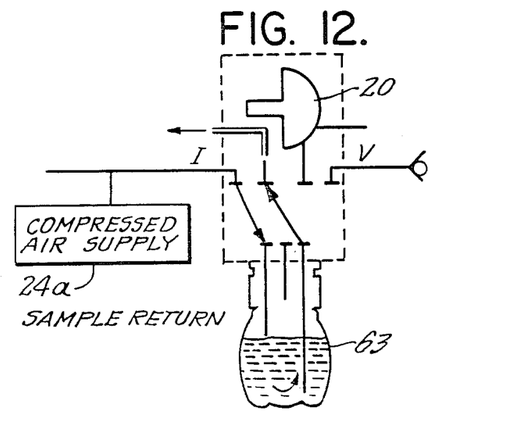
FIG. 12 is a similar schematic view showing the return of the remaining contents of a sample container after a sampling operation.

At this point in the disclosure, a brief discussion of FIGS. 10 through 15 is considered apposite. During normal operation, the valve spool 20 is positioned as shown in FIGS. 10, 13, 14 and 15, wherein process material may move without impediment between the flange members 13 and 14. When a sample is desired, the valve is positioned as shown in FIG. 11, wherein normal flow of the process material is blocked, and the material is flowed outwardly through the passage 24 and returned through the passage 23. As will more fully appear hereinafter, this position is possible only when a sample container has been positioned to receive this flow. When filled to a required level, the sample container is removed, the contents examined or tested, and the excess material is returned to the process line by reengaging the sample container and placing the valve spool 20 in the position shown in FIG. 12, wherein normal flow is blocked and through suction or purging with a source 24a of a compressed inert gas, such as nitrogen, the remaining portion of the sample is flowed back into the process line until the contents of the sample container have been substantially emptied.

Figure 2:
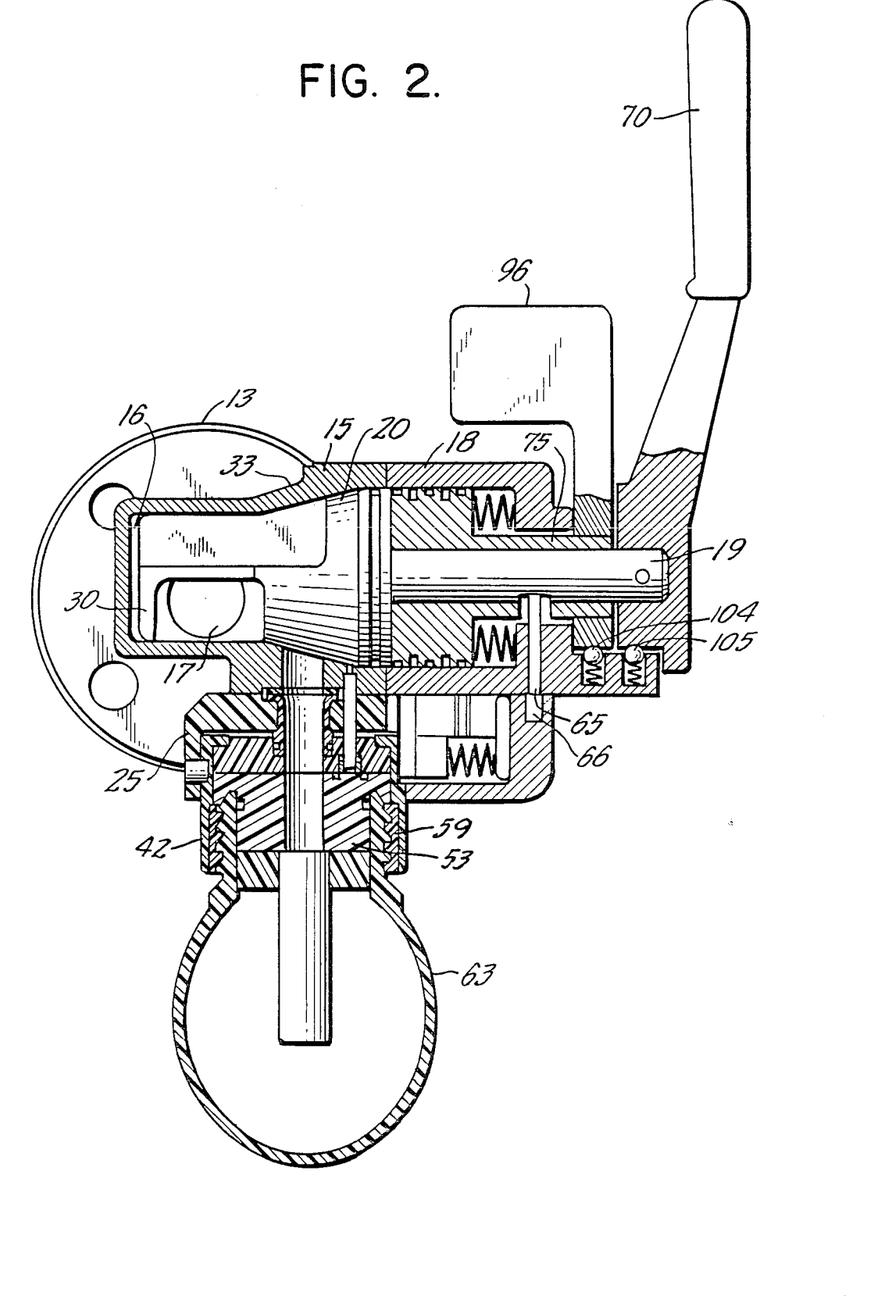
FIG. 2 is a schematic transverse sectional view thereof.
Figure 3A:
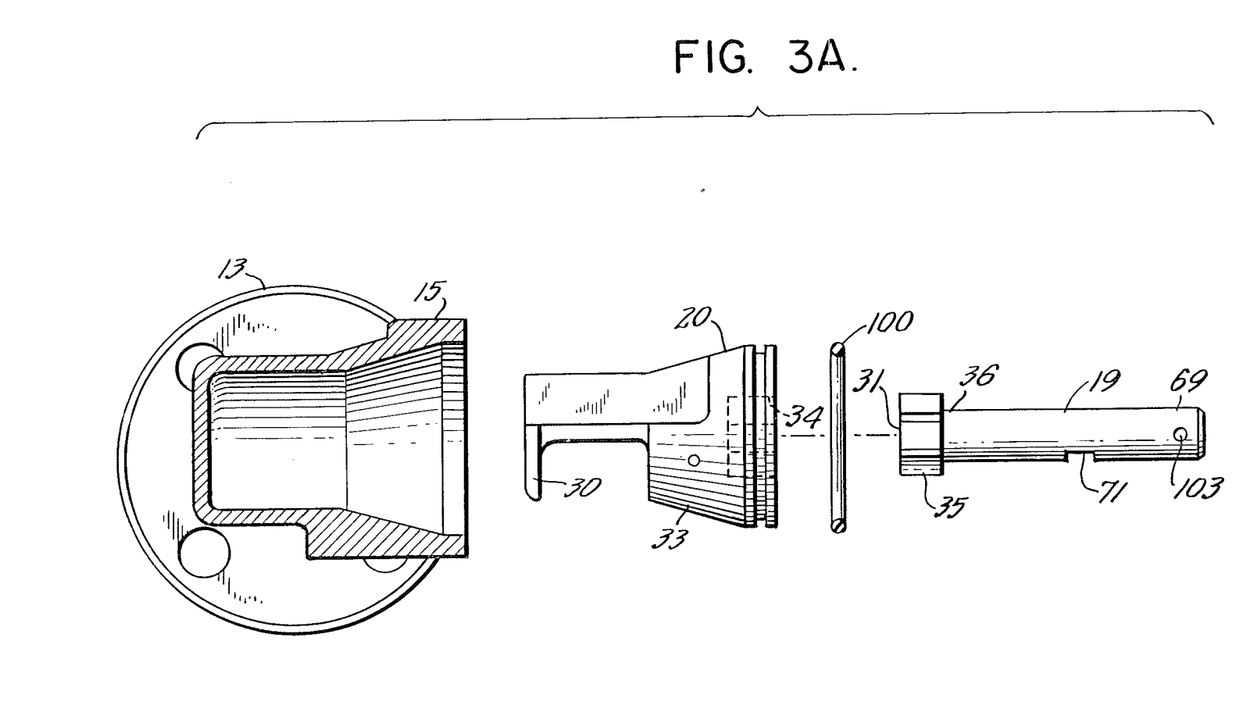
FIGS. 3A and 3B (hereinafter referred to collectively as FIG. 3) are exploded views in elevation, partly in section, showing details of a valving structure.
Figure 3B:
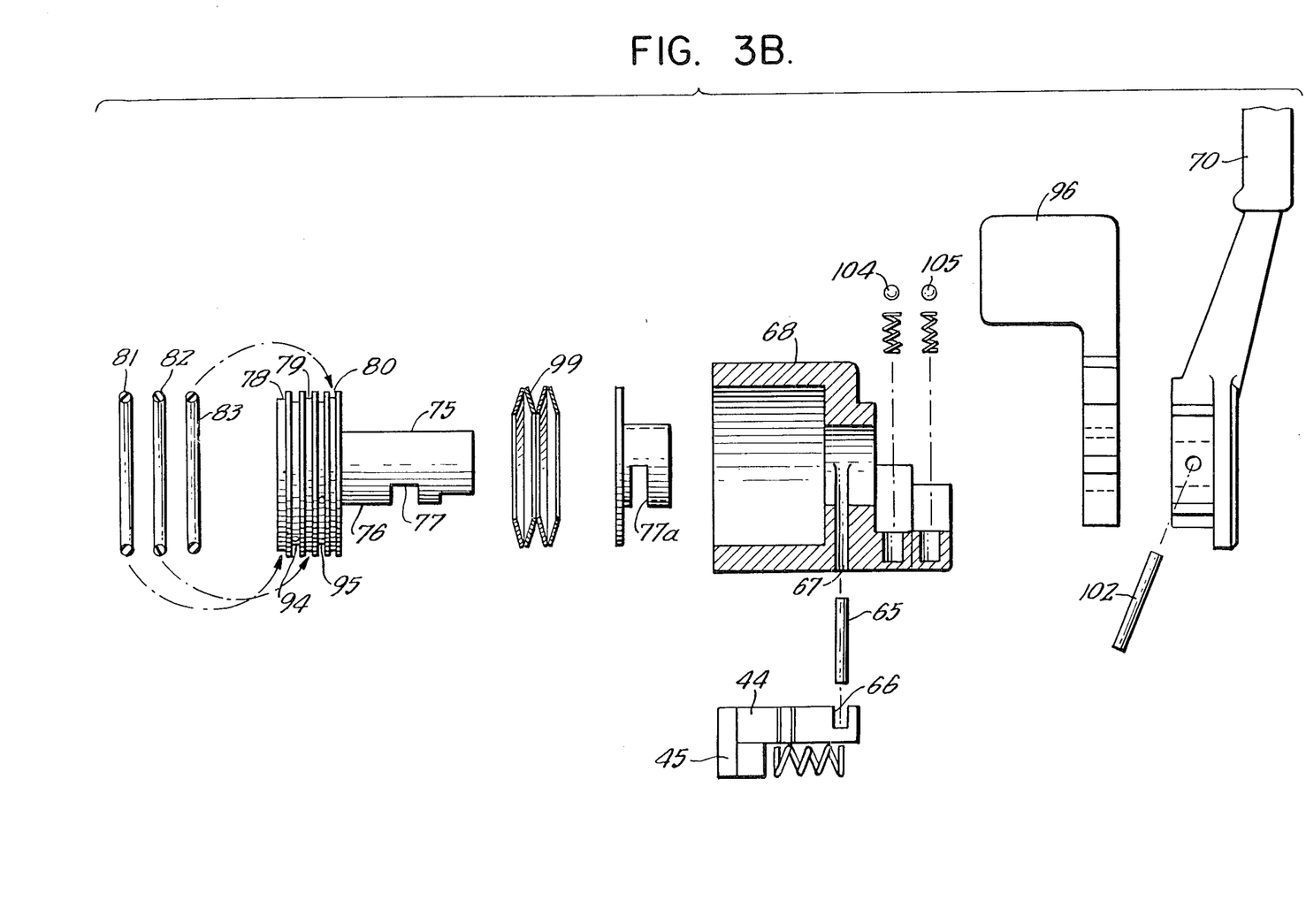

Referring to FIGS. 2, 3 and 4, a container engagement element 25 is preferably formed as a casting from chemically inert material, such as polytetrafluoroethylene. It include a cylindrical recess 40 in mounting member 41. A bottle closure member 42 selectively engages the recess 40 by means of a bayonet type flange 43. The member 42 is locked in position for sampling by a sliding lock plate 44 (FIG. 3) having a projection 45 selectively engaging a recess (not shown) in the flange 43. A pivotally mounted release lever provides for withdrawal of the lock plate if not otherwise inhibited.

Disposed within the member 42 is a cover plate 46 having countersunk openings 47 for the reception of fill tubes 48. A vent tube 49 is positioned in a counterbore 50 which also mounts O-ring 51 and a vent spacer 52. A bottle closure plate 53 abuts the cover plate 46b and includes an upper wall 54 and a cylindrical shank 55. A pair of counterbores 56 is aligned with the fill tubes, while a passage 57 communicates with the vent tube 49.

An O-ring 58 provides a rotational seal. An insert 59 is internally threaded at 60 and has an outer surface 61 seated against the surface 62 of the bottle closure member 42.

The sample container 43 is also of tetrafluoroethylene, and includes a main body 63 through which the contents may be viewed and an integrally molded threaded neck 64. Normally, after sampling, the container 43 is removed together with the bottle closure member with the cover plate 46 in closed condition wherein the withdrawn sample is completely sealed. Once removed, the cover plate may be rotated to opened condition for removal of the sample at a test or inspection location by syphoning or a like operation. However, in order to permit withdrawal of the lock plate 44, the vavle spool 20 must be in the position shown in FIG. 15. Referring to FIG. 3, this permits withdrawal of the latch 65 from the recess 66 through a bore 67 in the cover member 68.

Shaft 19, at its outer end 69, mount sample valve handles 70 which is capable of rotating through 270°. A recess 71 permits movement of the latch 72 when the spool 20 is in the position shown in FIG. 15.

Figures 6, 8:
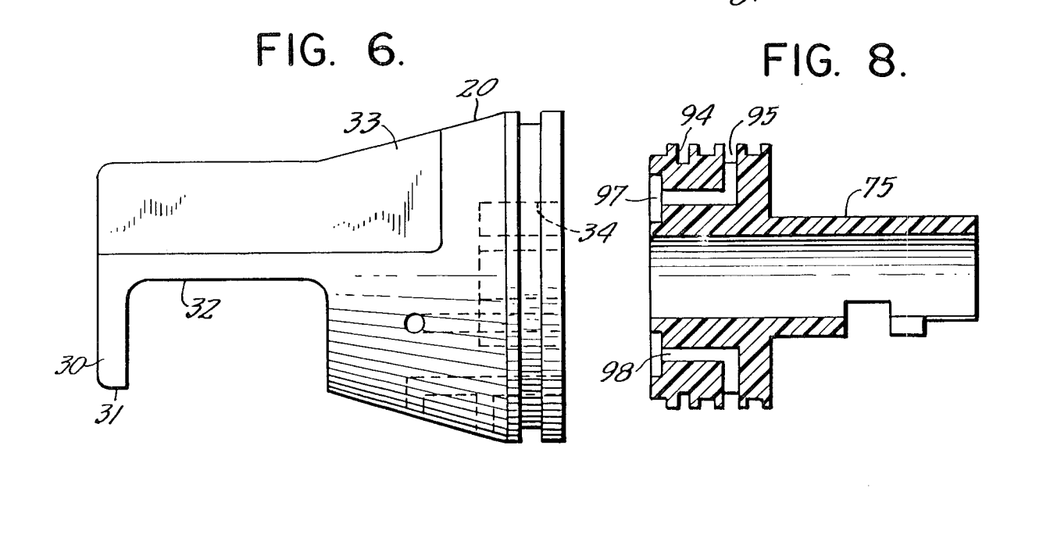
FIG. 6 is a side elevational view of the valve spool.
FIG. 8 is a sectional view as seen from the plane 8—8 in FIG. 7.
Figure 7:
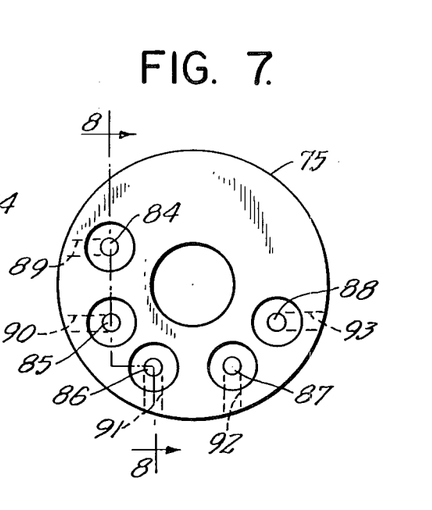
FIG. 7 is an end view in elevation of a second valve spool for controlling venting and purging of a sample container.
Figure 9:
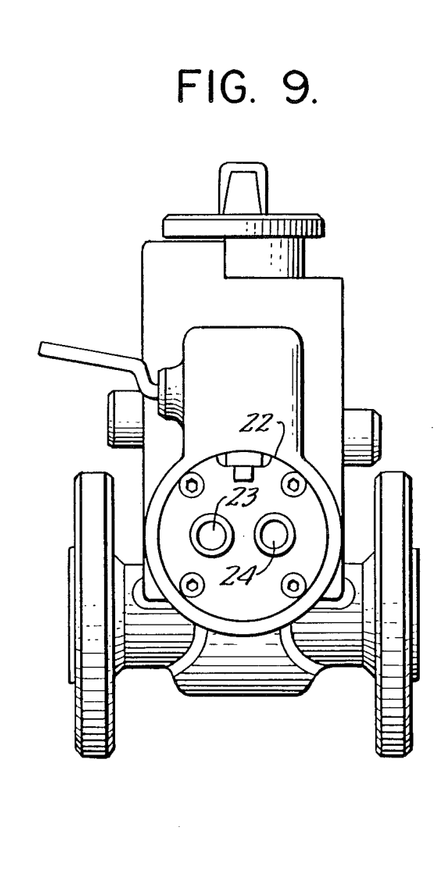
FIG. 9 is a bottom plan view of the embodiment with a sample container structure removed for purposes of clarity.

The venting and purging of the sample container 43 is accomplished by separate venting means best understood from a consideration of FIGS. 3, 7 and 8. A vent purge spool 75 includes a hollow shank 76 having a recess 77 alignable with the recess 77a when in concentric relation with the shaft 10. A plurality of sealing grooves 78, 79 and 80 are provided with O-rings 81, 82 and 83. Five longitudinal passages 84, 85, 86, 87 and 88 (FIG. 7) are disposed in generally radially arrangement and each has a laterally extending portion 89, 90, 91, 92 and 93. The passages communicate with one of first and second grooves 94 and 95 which in turn, communicate with one or the other of the valve fill tubes. The vent purge spool 75 is rotated by a lever 96 which moves through a 90° path of travel to selectively open a passage 97 communicating with a source of compressed inert gas (not shown) such as nitrogen, and a passage 98 leading to a source of collection of purge material (not shown), or vented to the ambient atmosphere.

Sealing about the vent purge spool is provided by Belleville springs 99 which urge the spool against an O-ring 100 bearing against the valve spool 20. The valve cover 101 mates with the shell 15 to form the chamber 16. The above-described structure is maintained in assembled condition by engagement of a pin 102 within a corresponding bore 103 in the shaft 19.

Separate sets of ball bearings 104 and 105 support the lever 96 and handle 70.

Figure 1:
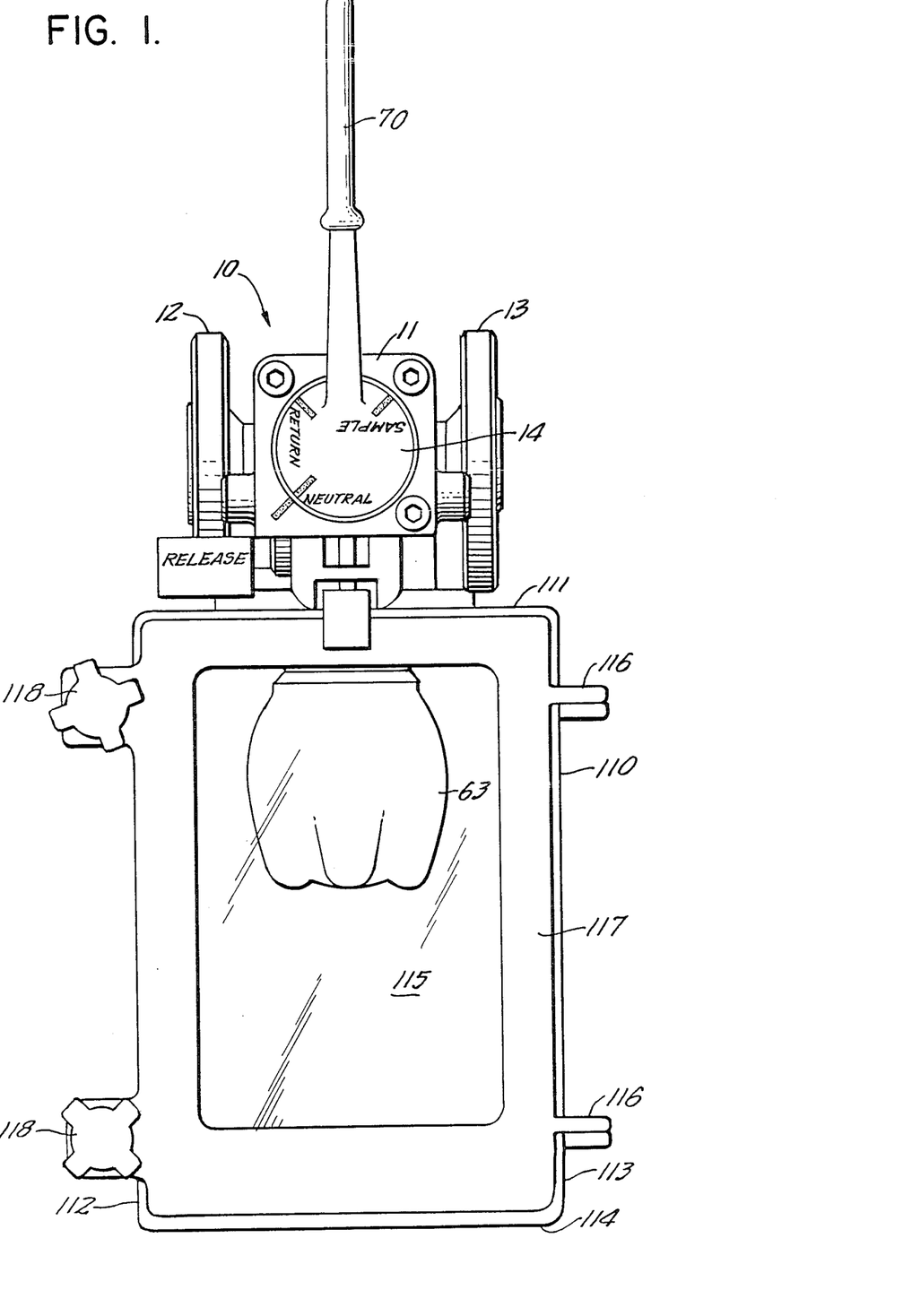
FIG. 1 is a front elevational view of an embodiment of the invention.

From a consideration of FIGS. 2, 3 and 4, it will be apparent that sampling is commenced with the sample valve handle disposed in the position shown in FIG. 1 indicated by reference character 106 (neutral). The vent purge lever is in the position shown in FIG. 3. The lock plate is then moved rightwardly as seen in FIG. 2 permitting engagement of a bottle closure and attached sample container with a combined axial and rotational motion on the part of the user.

Next, the sample valve handle is moved 180° to the position indicated by reference character 107 (sample) which corresponds to the schematic showing in FIG. 11. The filling of the container may be observed by the user and when the required amount of fluid has been obtained, the sample valve handle is again returned to neutral position, permitting removal of the sample container by pressing the release lever 107a (FIG. 4). When the sample container is removed, it will be in closed condition caused by relative rotation of the cover plate with respect to the bottle closure plate.

With the completion of removal of as much of the sample as may be required, the remainder of the sample can be returned to the process line by reversing the above-described procedure. After reengagement of the bottle closure, the sample valve handle is moved to the position indicated by reference character 108 (return) corresponding to the showing in FIG. 12. Next, the vent purge lever is rotated to open the passages 97 and 98 allowing inert nitrogen or other gas under pressure to enter the sample container and force the contents back into the process line. This operation, again, can be observed by viewing the translucent sample container.

Figure 13:
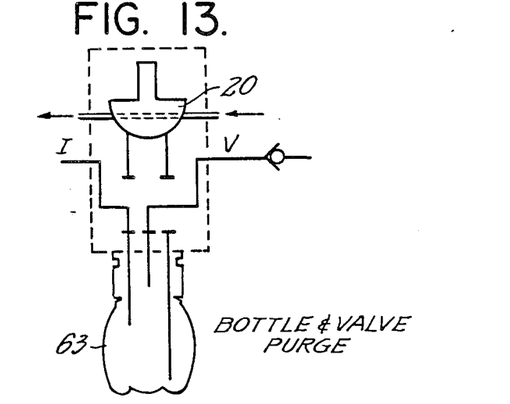
FIG. 13 is a similar schematic view showing pressurized purging of a sample container completing a sample return.
Figure 14:
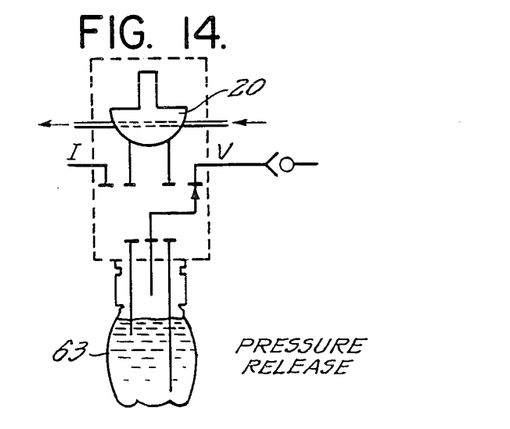
FIG. 14 is a similar schematic view showing the release of pressure after purging of a sample container.
Figure 15:
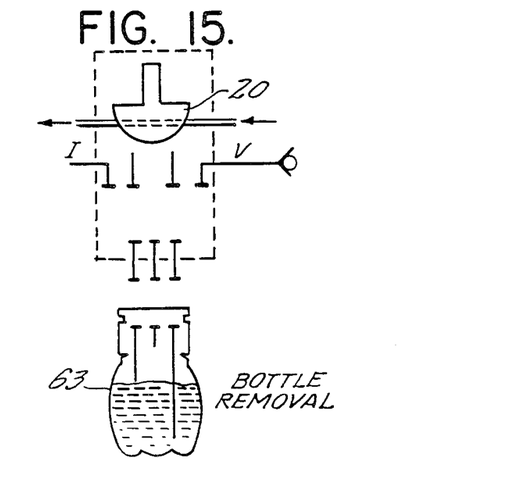
FIG. 15 is a similar schematic view showing sample container removal.

With the return of the sample, the sample valve handle is returned to neutral condition, and any remaining pressure is released (FIG. 10). As seen in FIG. 13, it is also possible to provide purging action by allowing the pressurized nitrogen to flow through the sample container independently of the process line.

FIG. 1 illustrates an optional safety enclosure 110 of particular value where process line pressures are substantially above atmospheric level. The enclosure is attached at an upper wall 111 in sealed relation to enclose the bottle closure. The enclosure is of generally rectangular configuration, including side walls 112 and 113, a lower wall 114, and a rear wall 115. A hinged interconnection 116 supports a windowed door 117 secured in closed position by wing nuts 118. The enclosed space within the enclosure is sufficient to permit entry of the hand of a user beneath the sample container for manipulation when the cover 117 is opened.

It will thus be seen that we have invented novel and highly useful improvements in chemical processed samplers in which there has been provided a structure for obtaining samples under otherwise relatively hazardous conditions caused by the presence of noxious, corrosive or other dangerous process materials, high operating temperatures and/or pressures. Means is provided for the safe disposition of surplus sampled material by returning it to the process line without the necessity of direct contact by the operator. Means is also provided for shielding the operator during the collection of the sample, without interfering with the control of the sample collected. Means is also provided for the purging of the sample container to facilitate subsequent cleaning for reuse.

We wish it to be understood that we do not consider the invention to be limited to the precise details of structure shown and set forth in this specification, for obvious modifications will occur to those skilled in the art to which the invention pertains.

We claim:

1. A chemical process sampler for use in extracting samples of material from a process line, comprising: a housing element adapted for in line positioning with respect to said process line, said housing element having laterally extending inlet and outlet passages for removal and return of samples to and from said process line; a valve element positioned within said housing having first, second and third positions of adjustment, a first position permitting continuous flow of material through said housing while maintaining said inlet and outlet passages in closed condition, a second position of which blocks flow of material directly through said housing, and directs said flow through said inlet and outlet passages; and a third position of which blocks said inlet passage while permitting flow through said outlet passage.

2. A process sampler in accordance with claim 1, further comprising a sample container element including an interlock element mounted upon said housing element and communicating with said inlet and outlet passages therein, said interlock element having a recess selectively engaging a sample container for the reception of a sample of process material thereinto; said interlock element having means preventing the positioning of said valve element in said second and third positions in the absence of a sample container in engaged condition with said interlock element.

3. A chemical process sampler in accordance with claim 2, further characterized in said interlock element including a bayonet type latch, said interlock element being permissively actuated by the rotational engagement of a sample container with said bayonet type latch.

4. A chemical process sampler in accordance with claim 3, further comprising a selectively engaged sample container having a hollow body defining an opening, a closure element engaged with said opening having bayonet engaging means on an outer surface thereof, an inlet and an outlet passage passing through said closure element having first and second members selectively, relatively rotable between first and second positions, in a first position of which said inlet and outlet passages are open, and in a second position of which said inlet and outlet passages are closed; rotational engagement and removal of said sample container with said bayonet type latch serving to relatively rotate said first and second members between said first and second positions.

5. A chemical process sampler in accordance with claim 4, further characterized in said bayonet type latch being manually operable for disengaging a sample container therefrom, operation of said latch being selectively inhibited by the positioning of said valve element in other than said first position.

6. A chemical processor sampler in accordance with claim 4, further characterized in said closure element being threadedly engaged upon said body to permit removal therefrom.

7. A chemical process sampler in accordance with claim 4 further comprising means for independently venting said sample container when in engaged condition relative to said interlock element.

8. A chemical process sampler in accordance with claim 4, further comprising means for selectively purging an engaged sample container by injecting an inert gas under pressure through said outlet passage.

9. A chemical process sampler in accordance with claim 4, further comprising a protective housing surrounding said sample container and secured to said interlock element, said housing having a sealable door permitting manual engagement therethrough of a sample container before and after a sampling operation.

* * * * *